US006995136B1

(12) United States Patent
Nelson et al.

(10) Patent No.: US 6,995,136 B1
(45) Date of Patent: Feb. 7, 2006

(54) PEPTIDE FRAGMENTS OF MURINE EPIDERMAL GROWTH FACTOR AS LAMININ RECEPTOR TARGETS

(75) Inventors: John Nelson, Belfast (IE); Brian Walker, Dundrum (IE); Neil McFerran, Belfast (IE); Patrick Harriott, Belfast (IE)

(73) Assignee: The Queen's University of Belfast, Belfast (GB)

( * ) Notice: Subject to any disclaimer, the term of this patent is extended or adjusted under 35 U.S.C. 154(b) by 0 days.

(21) Appl. No.: 09/673,785

(22) PCT Filed: Apr. 21, 1999

(86) PCT No.: PCT/GB99/01211

§ 371 (c)(1),
(2), (4) Date: Dec. 29, 2000

(87) PCT Pub. No.: WO99/54356

PCT Pub. Date: Oct. 28, 1999

(30) Foreign Application Priority Data

Apr. 22, 1998  (GB) .................................. 9808407

(51) Int. Cl.
*A61K 38/16* (2006.01)
*A61K 49/00* (2006.01)

(52) U.S. Cl. ............................ 514/8; 514/12; 530/328; 530/334; 530/335; 530/336; 530/344; 530/399; 435/7.1; 424/9.1

(58) Field of Classification Search ................. 514/15, 514/8, 12; 530/399, 328, 334, 335, 336, 530/344; 435/7.1; 424/9.1
See application file for complete search history.

(56) References Cited

U.S. PATENT DOCUMENTS 4,686,283 A    8/1987   Nestor, Jr. et al. .......... 530/327

OTHER PUBLICATIONS

Nelson et al., J. Biol. Chem. 271, 26179-26186 (1996).*
Baileie, J. R. et al: "Synthesis and receptor-binding activity of peptide fragments of epidermal growth factor" Biochem. Soc. Trans. (1989), 17(2), 409-10, 1989, XPOO2116635 p. 409, right-hand column; table 1.
McFerran, Neil V. et al: "A peptide molecular dynamics study correlates structure with function"Biochem. Soc. Trans. (1996), 24(1), 127s, 1996, XPOO2116636 p. 127s, left-hand column, paragraph 4.
Nelson, John et al: "Murine epidermal growth factor (EGF) fragment (33-42) inhibits both EGF-and laminin-dependent endothelial cell motility and angiogenesis" Cancer Res. (1995), 55(17), 3772-6, 1995, XP002116637 p. 228.
Nelson, John et al: Murine epidermal growth factor peptide (33-42) binds to a YIGSR-specific laminin receptor on both tumor and endothelial cells: J. Biol. Chem. (1996), 271(42), 26179-26186, 1996, XP002116638 p. 26183, left-hand colun, paragraph 3 p. 26186, left-hand column, last paragraph.

* cited by examiner

*Primary Examiner*—Jon Weber
*Assistant Examiner*—Chih-Min Kam
(74) *Attorney, Agent, or Firm*—Drinker Biddle & Reath LLP

(57) ABSTRACT

A peptide factor, its analogs and methods of using such peptide factor derived from murine epidermal growth factor peptide is disclosed wherein the peptide factor is modified to protect it from proteolytic degradation and the peptide binds to laminin receptors.

23 Claims, 1 Drawing Sheet

PEPTIDE FRAGMENTS OF MURINE EPIDERMAL GROWTH FACTOR AS LAMININ RECEPTOR TARGETS

BACKGROUND OF THE INVENTION

Figure 1A:
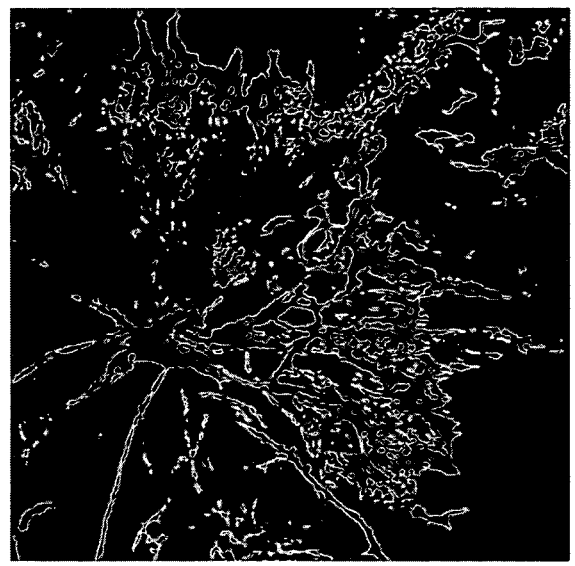

This invention relates to the use of (synthetic and modified) laminin receptor-targetted ligands for the treatment of angiogenic diseases such as proliferative retinopathies and metastatic cancer as well as for the treatment of *Candida* spp. infections, or parastic infestations such as *leishmania* and *trichomonas vaginalis*.

Laminin antagonists (which are anti-angiogenic) can be used to inhibit secondary tumour spread (by inhibiting tumour cell attachment) and to prevent growth of metastatic secondaries (by inhibiting neovascularisation). These antagonists could also be used to treat other angiogenic disorders (such as diabetic retinopathy).

Laminin agonists (which promote angiogenesis) could be used to treat retinopathy of prematurity, and could also be used to promote wound healing (for example in corneal epithelium).

Both the antagonists and the agonists would be expected to inhibit parasite binding to tissue surfaces and would thus prevent infection or infestation.

Angiogenic diseases are those disorders which are directly caused by, or complicated by the inappropriate growth of new blood vessels. The major angiogenic diseases include the common metastatic solid tissue cancers (breast, gastrointestinal, lung, prostatic, etc), diabetic retinopathy, neovascular glaucoma, rheumatoid arthritis and psoriasis. Angiogenesis is the rate-limiting step in the growth of secondary tumours; inhibition of their neovascularisation is known to stop their growth.

In this field it is already known that the native ligand of the 67 kDa laminin receptor (67LR) is encompassed by the linear sequence of amino acids 925–933 of the laminin β-1 (previously known as laminin B1 or b1) chain (numbering refers to the mature murine laminin β-1). Synthetic laminin β-1$_{925-933}$ (single letter amino acid code: CDPGYIGSR-NH$_2$) (SEQ ID NO: 1) has been shown to inhibit tumour establishment in mice, by inhibiting attachment of tumour cells to basement membranes. It has also been demonstrated that laminin β-1$_{925-933}$ inhibits angiogenesis in the chick.

However, synthetic laminin-derived peptide (laminin β-1$_{925-933}$) stimulates angiogenic events in mammalian cells (in which it acts as a pure 67LR agonist), making it useless as the basis of a human therapy.

It is one object of the present invention to provide a medicament to treat angiogenic diseases.

The present invention provides a peptide factor derived from murine epidermal growth factor (EGF) peptide for use in the preparation of a medicament for the treatment of angiogenic diseases.

The mechanism by which EGF derived peptides inhibit new blood vessel formation is through their antagonism of the high affinity 67 kDa laminin receptor (67LR) found on endothelial cells.

The peptides have the additional effect of inhibiting tumour cell attachment to basement membranes, and may be used to prevent solid cancer spread in cases where cancer cells have been identified circulating in the blood.

Modified peptides may be protected from proteolytic degradation by substitution of key residues with unnatural amino acid analogues at susceptible bonds, such as tyrosine analogues (at position 5) and arginine analogues (at position 9). The peptides may be capped at N- and C-termini (with acetyl and amide groups respectively) and at the thiol groups of the cysteines (with acetamido methyl groups).

Typically the peptide is an antagonist of the 67 kDa Laminin Receptor (67LR).

The peptide factor is based on amino acid residues 33 to 42 of murine epidermal growth factor (mEGF).

The amino acid sequence of mEGF-(33–42) is CVIGYS-GDRC (SEQ ID NO: 2).

Preferably the sequence of peptide factor is modified from the natural sequence to protect the peptides from protease attack.

Preferred substitutions include the use of tyrosine analogues at position 5 (SEQ ID NO: 3) and arginine analogues at position 9 (SEQ ID NO: 4).

Preferably the peptide factor is capped at the N terminal with an acetyl group (SEQ ID NO: 5).

Preferably the peptide factor is capped at the C terminal with an amide group (SEQ ID NO: 6).

Preferably the thiol groups of cysteines are capped with acetamido methyl groups.

In one embodiment the synthetic peptide has the sequence Acetyl-C-[S-Acm]-VIGYSGDR-C-[S-Acm]NH$_2$ (SEQ ID NO: 7)

A preferred tyrosine analogue is Tic-OH (SEQ ID NO: 8).

A preferred arginine analogue is Citrulline (SEQ ID NO: 9).

The structure of Citrulline and other potential arginine analogues are shown below.

Citrulline and Analogues

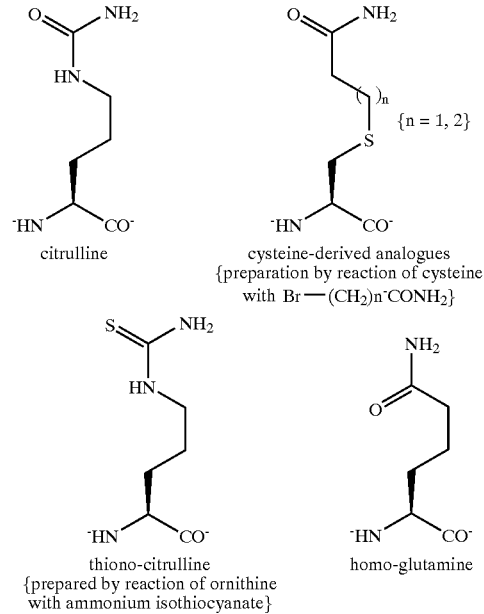

Preferably the peptide is truncated to a shorter peptide without losing its antagonistic character.

The invention further provides a peptide agonist.

The agonist may be the native sequence (single letter amino acid code:CDPGYIGSR-NH$_2$) (SEQ ID NO: 1) or may have the tyrosine substituted by any of a variety of tyrosine analogues such as the comformationally restricted Tic-OH (SEQ ID NO: 31) or 2',6'-dimethyl-beta-methyltyrosines (SEQ ID NO 10), 2-O-methyl (SEQ ID NO 11) and 2-O-ethyl-tyrosine and the like (SEQ ID NO 12).

The agonist may be useful in healing endothelial cell wounding.

For example, corneal endothelial cells can be damaged during cataract operations and this damage does not self-repair because these endothelial cells do not divide. Healing can only be effected by cell migration and spreading, and this may be promoted by the agonist.

In order to explore possible conformations for the parent mEGF$_{33-42}$ peptide, it was modelled using molecular dynamics. Based on these conformations a strategy has been predicted to provide proteolytic protection by being able to identify residues that are important to the maintenance of a three-dimensional conformation essential for 67LR recognition.

The following is a description of some examples of modifications and uses of the invention.

1. On the basis of the modelled structures, it was found that the arginine residue participated in H-bonding, and speculated that this charge may not be important. A peptide was synthesised based on mEGF$_{33-42}$, in which the arginine residue at position 41 was replaced by citrulline (an uncharged arginine mimetic with similar H-bonding potential). This peptide provided to act as a more potent 67LR antagonist and was found to be resistant to trypsin degradation.

2. Double substitution of tyrosine$_{37}$ with Tic-OH and arginine$_{41}$ with citrulline (SEQ ID NO: 13), to produce a mEGF$_{33-42}$-derived peptide resistant to both chymotrypsin-like and trypsin-like proteases.

3. Replacement of susceptible peptide bonds in mEGF$_{33-42}$ with protease-resistant peptide bond isosteres (such as thionopeptide or methylene amino bonds).

4. Conformationally restricted analogues may give improved potency due to the essential 3-dimensional conformation being stabilised. For example, it should be possible to increase the rigidity of the molecule by replacing each of the central glycine residues in turn by $\alpha,\alpha$-dialkyl substituted amino acids such as $\alpha$-amino isobutyric acid (AIB) (SEQ ID NO: 29) or aminocyclopropane carboxylic acid (ACPCA) (SEQ ID NO: 30). Alternatively, the helical turn (which we have identified as essential) could be stabilised by bridging with suitable intra-chain linkers, such as a disulphide bond between N- and C-terminal [D] or [L]-cysteines (SEQ ID NO 14).

EXAMPLE 1

The invention is demonstrated with reference to the following figures wherein.

Figure 1B:

FIG. 1a depicts a flat mount retina showing the effects of ROP and FIG. 1b depicts a retina from laminin-agonist treated mouse showing re-canalisation of vessels.

TREATMENT OF RETINOPATHY OF PREMATURITY (ROP)

Severely premature babies are at risk of developing retinopathies due to their being exposed to high oxygen levels post-partum. This life-saving intervention compensates for poor lung development but has the unfortunate side-effect of causing unnaturally hyperoxic conditions in the retina. The direct effect of this is to remove the normal hypoxic cues for endothelial migration, resulting in inhibition of capillary growth and vaso-obliteration. When these babies are returned to room air, hypoxic stimuli are restored and retinal angiogenesis is again induced. However, the newly induced angiogenesis is chaotic and uncontrolled, often resulting in abnormal penetration of vessels into the vitreous (see FIG. 1a, below). It is the uncontrolled growth of these blood vessels that ultimately leads to loss of visual activity.

It has now been shown that laminin agonist treatment can reverse the effects of both hyper-oxic induced vaso-ablation as well as norm-oxic-induced angiogenesis in a murine model of retinopathy of prematurity (ROP). In this model, development of ROP can be prevented by treatment of neonates with daily injections (intraperitoneal) of 10 $\mu$g of synthetic laminin $\beta$-1$_{925-933}$ (also referred to as laminin B1$_{925-933}$, single letter amino acid code:CDPGYIGSR-NH$_2$) (SEQ ID NO: 1). See FIG. 1b in comparison with 1a. Treatment with laminin agonist (FIG. 1b) prevents the uncontrolled angiogenic response of ROP (FIG. 1a) and promotes re-canalisation of areas of vaso-obliteration.

The invention is demonstrated with reference to the following figures wherein FIG. 1a depicts a flat mount retina showing the effects of ROP FIG. 1b depicts a retina from laminin-agonist treated mouse showing re-canalisation of vessels.

Murine Model of Proliferative Retinopathy

Litters of 7 day old C57-BL/6J mice, together with their nursing dams, are exposed to 80% oxygen in an incubator maintained at 23° C. and with a gas exchange of 1.5 L/min for 5 days according to the protocol described by Stitt et al. (1998). On postnatal day 12 (P12) the animals are returned to room air and sacrificed at various times posthyperoxia. Animals are treated with daily i.p. injections of either laminin agonists (10 $\mu$g per head per day) or vehicle control. Groups of room air controls are maintained in parallel with hyperoxia-exposed animals. Home Office project and personal licenses are held for this work. All animals are housed and maintained in accordance with the ARVO regulations for animal care in research.

Animals are sacrificed at pre-determined key stages in the vaso-obliteration (P7–P12), ischaemia (P12 onwards) and vaso-proliferative responses (P 12–21). At sacrifice, terminally anaesthetised animals have a single eye enucleated and the retina removed to be snap-frozen for later RNA-extraction (see below). The fellow eye is either perfused with fluorescein dextran or enucleated and fixed in 4% paraformaldehyde for histology, immunohistochemistry and in situ hybridisation.

Alternative Uses

1. Treatment of Corneal Wounds

The cornea is a delicate transparent structure. Being avascular, corneal wound healing depends upon local self-renewal of the corneal epithelium. This, in turn, depends upon the presence of a mitogenically functional stem cell population ('limbal cells'), which produce replacement cells that migrate and desquamate at the denuded area. Damage to these underlying stem cell populations causes inappropriate re-epithelialization by conjunctival cells followed by matrix deposition and scar formation. The damaging agent may be corrosive chemical or heat burns, erosion by contact lenses, Stevens Johnson disease.

It is known that transplantation of limbal cell autografts from the unaffected eye can restore a stable healing of the corneal epithelium (Kenyon et al., 1996). It has been proposed that harvesting small samples of limbal stem cells, followed by serial culture in vitro would provide greater chance of success (particularly when both eyes are affected) De Luca, et al., 1997). However, with both protocols, correct uptake and controlled migration of these grafted cells into the corneal epithelium has not been optimised.

We propose that laminin agonists could be used to stimulate the migratory response of the cells prior to grafting, or alternatively topical application of laminin agonists to the wound site could be used to direct migration of the grafted cells to the correct (denuded) area of the cornea.

2. Some microbial pathogens such as *Candida albicans*, express 67LR and use this as a means of attaching to human basement membranes. It is conceivable that such infections could be abolished by treatment with $mEGF_{33-42}$-derived peptides, which would prevent the microbes from adhering to the host.

EXAMPLE 2

Peptide Study

The purpose of the investigation was to determine the molecular target of $mEGF_{(33-42)}$ and to identify the amino acids that are essential for receptor recognition. In addition, the key residues which confer laminin antagonism on $mEGF_{(33-42)}$ were examined.

Two lead compounds were investigated; synthetic laminin β-1 sequence CDPGYIGSR-$NH_2$ (SEQ ID NO: 1) and $mEGF_{(33-42)}$ sequence AcC(Acm)-VIGYSGDRC-(Acm)-$NH_2$ (SEQ ID NO: 2). Bearing in mind the pure antagonism of the murine EGF peptide, the aims of this study were to identify the key residues responsible for these contrasting activities using alanine scanning, in the context of developing anti-angiogenic drugs for retinopathy treatment.

In addition, using residue exchange between the two peptides and molecular modelling to predict three-dimensional structure, we wished to further investigate the role of individual $mEGF_{(33-42)}$ residues in laminin antagonism. A logical series of peptides was synthesised and screened for receptor interaction, cell adhesion and motility properties (Table 1a and 1b).

Materials and Methods

Peptide Synthesis

Peptide sequences based on and $mEGF_{(33-42)}$ were synthesised on a model 432A peptide synthesizer (Applied Biosystems, Warrington, UK), using standard solidphase Fmoc procedure (Fields 1990). Synthesis of the peptides required successive additions of derivatized amino acids to form a linear product.

Peptides were purified after synthesis using reverse phase HPLC and purity confirmed by automated amino acid analysis and electrospray mass spectrometry. All peptide sequences were stored in the presence of desiccant at −20° C. until required for biological assay.

Laminin Receptor Antibody Production a. Preparation of MAPs

The peptide sequence (PTEDWSAQPATEDWSAAPTA) (SEQ ID NO: 15), corresponding to the COOH-terminal end of the human laminin receptor, was used as the antigen template. Derivation of the peptide, based on a CN-Br cleavage fragment of the cDNA sequence encoding human laminin receptor, has been described elsewhere (Wewer et al 1986). The antigen was synthesised as an octomeric peptide derivative (MAPs) using automated Fmoc procedure (Tam 1988).

TABLE 1a

| Peptide substitution | | | | | | | | | | |
|---|---|---|---|---|---|---|---|---|---|---|
| $mEGF_{(33-42)}$ (SEQ ID NO: 7) | acetyl | ACM Cys | Val | Ile | Gly | Tyr | Ser | Gly | Asp | Arg | ACM Cys—$NH_2$ |
| I (SEQ ID NO: 16) | acetyl | ACM Cys | Val | Ile | Gly | Tyr | Ile | Gly | Asp | Arg | ACM Cys—NH2 |
| II (SEQ ID NO: 17) | acetyl | ACM Cys | Val | Ile | Gly | Tyr | Ser | Gly | Ser | Arg | ACM Cys—$NH_2$ |
| III (SEQ ID NO: 18) | acetyl | ACM Cys | Val | Ile | Gly | Tyr | Ile | Gly | Ser | Arg | ACM Cys—$NH_2$ |
| IV (SEQ ID NO: 19) | acetyl | ACM Cys | Val | Ile | Gly | Tyr | Ser | Gly | Asp | Cit | ACM Cys—$NH_2$ |
| V (SEQ ID NO 20) | acetyl | ACM Cys | Val | Ile | Gly | OH Tic | Ser | Gly | Asp | Arg | ACM Cys—$NH_2$ |

TABLE 1b

| Peptide substitution (alanine scanning) | | | | | | | | | | | |
|---|---|---|---|---|---|---|---|---|---|---|---|
| $mEGF_{(33-42)}$ (SEQ ID NO: 7) | acetyl | ACM Cys | Val | Ile | Gly | Tyr | Ser | Gly | Asp | Arg | ACM Cys—$NH_2$ |
| VI (SEQ ID NO: 21) | acetyl | ACM Cys | Val | Ala | Gly | Tyr | Ser | Gly | Asp | Arg | ACM Cys—$NH_2$ |
| VII (SEQ ID NO: 22) | acetyl | ACM Cys | Ala | Ile | Gly | Tyr | Ser | Gly | Asp | Arg | ACM Cys—$NH_2$ |
| VIII (SEQ ID NO: 23) | acetyl | Ala | Val | Ile | Gly | Tyr | Ser | Gly | Asp | Arg | ACM Cys—$NH_2$ |
| IX (SEQ ID NO: 24) | acetyl | ACM Cys | Val | Ile | Gly | Tyr | Ser | Gly | Asp | Arg | Ala—$NH_2$ |
| X (SEQ ID NO: 25) | acetyl | ACM Cys | Val | Ile | Gly | Tyr | Ala | Gly | Asp | Arg | ACM Cys—NH2 | b. Immunisation Schedule

A pre-immune test bleed (5 ml) was obtained from the marginal ear vein of a male New Zealand White rabbit (3.2 kg). The bleed was allowed to clot for 2 h at room temperature after which its edge was detached from the wall of the collection vessel. The clot was then allowed to contract overnight at 4° C. Serum was then removed and the residual material pelleted out by centrifugation (10 min at 2,500 g). Extracted serum (3.5 ml) was then frozen at −20° C. until required.

Immunogen was prepared by the emulsion of MAPs (0.5 g antigen in 0.5 ml PBS) in an equivalent volume of adjuvant (Alum Imject; Pierce, Chester, UK). The animals immune system was primed by introducing immunogen (50 µg) through subcutaneous injection at different sites on the animals back. The rabbit was boosted by both subcutaneous and intramuscular injection, 21 days after priming, using an increased dose of immunogen (800 µg). Subsequent boosts were performed by intramuscular injection after a further 14 days (800 µg immunogen), and thereafter at 21 day intervals. Test bleeds were taken 2 days after each boost and the serum extracted as described above. The animal was boosted and bled a total of three times.

c. Enzyme-Linked Immunoabsorbent Assay

ELISA was used to determine the specificity of the antibody prepared against the synthetic MAPs peptide and to determine the efficacy of binding with respect to that of the linear precursor.

Peptides were dissolved in distilled water and diluted to 10 µg/ml in coating buffer. Aliquots (100 µl) of either linear or MAPs peptide were then added to the wells of microtitre plates (Microtest III; Becton Dickinson Ltd., Oxford, UK) and incubated overnight at 37° C. The wells were then rinsed with 100 µl wash buffer and air dried. Excess adsorption sites were blocked (1 h incubation at 22° C.) by the addition of 10% casein in PBS (0.1 ml/well). Subsequent to the removal of casein solution by aspiration, wells were again rinsed with wash buffer and air dried.

Antisera or pre-immune sera were then serially diluted in PBS and 100 µl of each incubated in peptide coated wells for 1 h at 37° C. After rinsing (0.1 ml wash buffer), 100 µl per well of 5 µg/ml secondary antibody (horse-radish peroxidase-conjugated goat anti-rabbit IgG; Amersham International, Aylesbury, UK) was added to each well and the plates incubated at 37° C. for 1 h.

Wells were again rinsed with wash buffer and 0.1 ml substrate solution (TMB peroxidase) added to each. The plate was then incubated at 22° C. for 30 min and the colour reaction stopped by the addition of 0.5M $H_2SO_4$ (0.1 ml/well). Absorbence was measured at 450 nm on a Titertek Multiscan plate reader.

d. Purification of IgG Fraction

Anti-laminin receptor antiserum was purified using immobilised protein G-sepharose columns (Pharmacia Biotech, Uppasla, Sweden). The columns were equilibrated with 20 ml sodium phosphate buffer (pH 7.0). Antiserum was diluted 1:4 in the same buffer and a 1 ml aliquot loaded onto the column (flow rate 150 ml/h, fraction size 2.5 ml). After exclusion of the unbound fraction, as determined by absorbence at 280 nm, the IgG component of the antiserum was eluted with 0.1M glycine-HCl (pH 2.7), into tubes containing 0.1 ml Tris (1M), pH 9.0. The eluted IgG fractions were bulked and stored at 20° C. until required.

Maintenance of Cell Cultures

Cancer and endothelial cells were maintained in either DMEM (T47-D) or RPMI (SK HEP-1) media, supplemented with 10% FCS, 100 IU/ml penicillin and 100 µg/ml streptomycin. Cells were incubated at 37° C. in a humidified atmosphere of 95% air: 5% $CO_2$ and media refreshed as required. Cultures (at 80–85% confluence) were routinely passed on removal from monolayer by the action of trypsin (0.25%) and EDTA (0.02%) in CFS.

The viability of cell populations following trypsinisation was determined by the trypan blue vital dye exclusion test. Populations confirmed as being in excess of 95% viable were used in all studies.

Media were screened for possible bacterial or fungal contamination by incubating 1 ml aliquots with both nutrient and Saboraud dextrose broths (Oxoid Ltd., Basingstoke, UK). Cell populations were routinely monitored for subclinical infections by periodically culturing in the absence of antibiotics.

Both cell lines and media were examined for the presence of contaminating *Mycoplasma* spp. by the method of Chen (1977).

Determination of Cell Numbers

Single cell suspensions were quantified using an automated counter (Coulter Electronics, Harpenden, UK). A 1 ml aliquot of cell suspension was diluted 1 in 20 in Isoton and 0.5 ml samples counted. The mean of 5 counts was taken and the total number of cells determined. Estimates of cell number were confirmed by counting in a haemocytometer.

For microtitre end-point assays, cell numbers were estimated from the crystal violet staining index of the cell line (Kanamaru and Yoshida 1989). Briefly, after removal of media from the assay system cells were fixed with formaldehyde (10% in PBS), and washed with distilled $H_2O$. Aliquots (100 µl) of crystal violet solution (0.1% in distilled $H_2O$) were added to each well and the plates allowed to stand for 30 min. Excess stain was removed by rinsing with distilled $H_2O$ (3×100 µl). The wells were then air-dried and the remaining crystal violet extracted with 100 µl acidified methanol. Absorbance at 620 nm was determined using a Titertek Multiscan spectrophotometer.

Proliferation Assays

The effects of synthetic peptides and growth factors on the growth of breast cancer and endothelial cells were determined as detailed.

Exponentially growing cells were harvested by trypsinisation, as previously described. After rinsing and resuspending in the relevant culture media (containing 10% FCS), the cells (100 µl aliquots) were dispensed into 96-well microtitre plates at a population density of $2×10^4$ cells/well (6 wells per experimental condition). Cells were the incubated for 24 h at 37° C. after which the media was removed and the wells rinsed with CFS (3×100 µl), to rid the plates of cells in suspension. Media was then replaced with that containing the relevant controls or treatment supplements as detailed in individual experiments.

Cell numbers were evaluated spectrophotometrically at 620 nm, over the period of assay, after fixing with 10% formaldehyde and staining with crystal violet.

Proliferative responses were analysed using the Wilcoxan Rank test and significant differences at the $p<0.05$ level, defined. Results of all growth studies were confirmed in at least 3 individual experiments.

Laminin Attachment Assay

Non-tissue culture grade 96-well plates, coated with 2.5 µg murine laminin in 50 µl CFS per well, were air-dried overnight at room temperature. Preliminary experiments indicated that cell attachment was concentration dependent; maximal binding occurred at a laminin coating of 2.5 µg/well. After rinsing with CFS (100 µl), the plastic was saturated with casein (0.2% in CFS). Plates were incubated at room temperature for 45 min then washed extensively with CFS (3×100 µl).

After removal of culture media, cells were detached from monolayers by the action of EGTA (0.02% in CFS) at 37° C. The cells were then centrifuged at 800 g for 2 min and the pellet resuspended in DMEM (T-47D) or RPMI (SK HEP-1).

Cells, at a population density of $10^6$ cells/ml, were then aliquoted (1 ml) into microfuge tubes containing the individual peptide sequences and incubated for 1 h at 37° C. The cells (100 µl aliquots) were then added to the pre-coated multi-well plates and incubated for a further 60 min. Incubation media were removed and the wells washed with CFS (3×100 µl) to rid the plates of non-adherent cells.

Attached cell numbers were evaluated spectrophotometrically at 620 nm after fixing with 10% formaldehyde and staining with crystal violet.

Attachment to $mEGF_{(33-42)}$

That $mEGF_{(33-42)}$ bound to the 67 kDa laminin receptor was demonstrated using a biotinylated derivative of the peptide (Acetyl-C-[S-Acm]-VIGYSGDR-C-[S-Acm]-K-[$N^\epsilon$-biotin]-amide) (SEQ ID NO: 26) and a modification of the above laminin attachment assay.

Briefly, 96-well plates were coated with 100 µl/well streptavidin (5 µg/ml in carbonate buffer pH 9.6) and following an overnight incubation at 37° C., wells were washed with CFS (3×100 µl) and the plastic blocked with casein (0.2% in CFS). The plates were then incubated at room temperature for 45 min and washed with CFS as previously detailed. Biotinylated $mEGF_{(33-42)}$ in CFS was then aliquoted into the wells (0.1 ml of 100 µM) and the plates incubated for 3 h at 37° C.

After a further block with 0.2% casein, the wells were washed with CFS (3×100 µl aliquots). Plates were kept at 4° C. and used within 2 h.

Cells were prepared as above and pre-incubated for 1 h at 37° C. with serial dilutions of anti-laminin receptor polyclonal (see below) or anti-EGF (R1) receptor monoclonal antibodies. Subsequent procedures were as detailed for the laminin attachment assay.

Laminin Receptor Binding Determinations a. Radiolabelling of Laminin $^{125}$I-laminin was prepared using $^{125}$I-labelled sodium iodide (Amersham, UK) and immobilised chloramine-T (Iodobeads; Pierce, Ill.). Prior to use, the beads were washed with 500 µl phosphate buffer (pH 6.5) to remove excess reagent from the support. These were then allowed to air dry and individual beads added to a solution of carrier free Na$^{125}$I, diluted with iodination buffer (phosphate buffer pH 7.4). The beads were allowed to equilibrate for 5 min.

Laminin (10 µg in 10 µl) was then diluted into the iodination buffer and the system incubated at 20° C. for 15 min. The solution was then removed from the reaction vessel and excess Na$^{125}$I and unincorporated $^{125}$I$_2$ separated from the iodinated protein by gel filtration on a GF-5 exclusion column (Pierce, Ill.). Iodinated laminin fractions were recovered at a specific activity of approximately 1.2 mCi/mg protein (864 Ci/mmol).

b. Competition Binding Estimation

Near confluent cultures of T47-D or SK HEP-1 cells were removed from monolayer with 0.02% EGTA and passed through a G-25 syringe needle to produce single cell suspensions. Aliquots of each cell type ($10^6$ cells/ml) were dispensed into separate Ependorf tubes (1 ml each) and pelleted. The cells were then resuspended in 1 ml ice-cold RPMI (SK HEP-1) or DMEM (T47-D) containing 0.1% BSA and either laminin or synthetic peptide at the concentrations indicated. Iodinated laminin was then added to each cell suspension to give a final $^{125}$I-laminin concentration of 0.1 nM (approximately 50,000 cpm). These mixtures were incubated overnight at 4° C.

The tubes were then microfuged at 10,000 g and the supernatant removed. After washing the pellet with 500 µl CFS, the remaining radioactivity was determined using a gamma radiation counter. Non-specific binding was determined by incubating cells with a 1000-fold molar excess of unlabelled laminin. All estimations were carried out in triplicate.

$IC_{50}$ (concentration of unlabelled peptide required to produce 50% inhibition of radioligand binding) and $EC_{50}$ (effective concentration for 50% inhibition of cell attachment) values were calculated using the Grafit curve-fitting programme (Erithacus Software, London, UK).

Migration Assays

The method used was basically as described by Albrecht-Buehler (1977). Briefly, coverslips (22×22 mm) were treated in 5% detergent (7×; ICN Biomedicals) and washed in alcohol to remove grease. After drying, they were immersed in gelatin solution (Sigma, 300 Bloom; 0.5 g in 300 ml distilled $H_2O$) for 10 min. The coverslips were then dried by placing in a 70° C. oven for 45 min.

Colloidal gold suspension was prepared by adding 11 ml distilled $H_2O$ and 6 ml $Na_2CO_3$ (36.5 mM) to 1.8 ml $AuHCl_4$ (14.5 mM). The mixture was heated to 95° C. at which point 1.8 ml of freshly prepared 0.1% formaldehyde solution was added; the temperature was maintained at 95° C. A suspension of colloidal gold was formed which was brown to absorbed light and blue to transmitted light.

The gold suspension, was then added to petri dishes containing individual coverslips and the plates incubated at 37° C. for 45 min. After washing with CFS (3×4 ml) to remove unattached gold particles, the coverslips were transferred to 6-well cluster dishes and UV sterilised.

Endothelial cells (SK HEP-1 and BRCE) in culture media (0.3 ml) were seeded onto the coverslips at an approximate density of $5\times10^3$ cells per well. The cells were allowed to plate down for 2 h at 37° C. after which the treatments were added. Assay systems were maintained for a further 18 h after which the cells were fixed using 3% gluteraldehyde in cacodylate buffer (pH 7.2).

The assays were examined using a Leica DM1RB phase contrast microscope and Q500MC image analysis system incorporating a JVC TK-1280E colour camera (Leica, Milton Keynes, UK). The track images of at least 30 cells were videocaptured and the area (representing migration response) determined for each. Statistical analysis of these areas was then carried out using Macintosh Instat software to perform both Kruskal-Wallis analysis of variance and Mann-Whitney U-tests in order to compare the treatment groups with controls.

Results

Proliferative Response

All peptides were examined for their ability to influence the growth of T47-D and SK-Hep 1 cell lines. At concentrations of peptide up to 100 µM, no significant effects were observed in either cell line.

Mechanism of Action

It had shown previously that $mEGF_{(33-42)}$ could inhibit the EGF-stimulated angiogenic response in the early chick as well as blocking the basal and EGF-stimulated motility of primary and established endothelial cells.

During the present study it is shown that mEGF$_{(33-42)}$ also inhibits the angiogenic effects of laminin (Nelson et al 1995). Furthermore, it is demonstrated that the anti-angiogenic effects of mEGF$_{(33-42)}$ are mediated solely through the high affinity 67 kDa laminin receptor (67-LR) and not through the EGF receptor.

The study also confirms that mEGF$_{(33-42)}$, Lam.β-1$_{(925-933)}$ and laminin are equipotent in $^{125}$I-laminin displacement receptor assays, and that both of the small peptidal ligands have similar potencies in specific laminin cell attachment assays.

In addition, it is shown that the commonly used chick angiogenesis models are not appropriate to the study of laminin mediated human angiogenesis: although it is confirmed that Lam.β-1$_{(925-933)}$ acts as a partial laminin antagonist in chick, it was found to be a pure agonist in mammalian cell lines. This is a highly significant point given that pharmaceutical companies (such as Angiotech, Vancouver, BC) are using the chick CAM assay as the sole screening method for the discovery of anti-angiogenic lead compounds. This may be inappropriate for use in human disease.

This study is the first to show that the YIGSR-receptor is, in fact, the 67 kda high affinity laminin receptor (67-LR). In collaboration with Professor Archer's team at the Department of Ophthalmology, Royal Victoria Hospital, Belfast, it has been determined that the 67-LR is preferentially expressed in new vessels during oxygen-induced retinopathy in neonatal mice.

Peptide Antagonist Development

The N-terminus of Lam.β-1$_{(925-933)}$ is not necessary for receptor recognition and the agonist activity of YIGSR (SEQ ID NO: 28) peptide (Ostheimer et al 1992, Kawasaki et al 1994).

However, alanine scanning of the starting peptide (mEGF$_{(33-42)}$) indicated that residues at position 1,2,3, and 6 (peptides VI, VII, VIII and X respectively) (SEQ ID NO: 21, 22,23, AND 25 respectively), are essential for receptor mediated activities as determined by $^{125}$I-laminin displacement and cell attachment to laminin through the 67-LR. Substitution of these individual residues by alanine leads to a dramatic decrease in receptor affinity observed as an increased IC$_{50}$ (Table 1b) and a parallel decrease in their ability to block adhesion to laminin (increased EC$_{50}$; Table 1b). Characterisation of these analogues with regard to effects on motility, largely confirmed these findings although there was one exception; peptide VIII (SEQ. ID NO: 23). Results from the migration assay identified this sequence (alanine for cysteine (P1)) as being a weak laminin agonist despite there being a much reduced response in the other two assays. It is suggested that this peptide may influence laminin receptor mediated migration through an alternative mechanism (Scott 1997).

Substitution at P10 (alanine for cysteine (peptide IX) (SEQ. ID NO:24)) retains both receptor binding and adhesion displacing activities but has the agonism of Lam.β-1$_{(925-933)}$, which also lacks the C-terminal cysteine, and suggests that this cysteine is not essential for receptor recognition, but is required for antagonism of mEGF$_{(33-42)}$.

Studies have reported that the positive charge offered by arginine (P9) is essential for the biological activity of Lam.β-1$_{(925-933)}$ (McKelvey et al 1991, Kawasaki et al 1994). Glutamate substitution for arginine generates a negative charge at this position with corresponding loss of biological activities (Kawasaki et al 1994).

However, the substitution of arginine (P9) with positively-charged lysine (McKelvey et al 1991) also results in complete loss of ligand binding and biological activities, suggesting that the mere presence of a positive charge at this position is, in itself, insufficient for receptor recognition. This modelling studies suggest that H-bonding of the guanidino group of the arginyl residue to the aromatic sidechain of the tyrosyl residue (P5) in the consensus sequence GYXGXR (SEQ ID NO: 27) presents an acceptable motif for 67-LR activation by both mEGF$_{(33-42)}$ and Lam.β-1$_{(925-933)}$.

Substitution of tyrosine (P5) with a conformationally restricted mimetic (tetrahydroisoquinoline-3-carboxylic acid; Tic-OH) in peptide V (SEQ ID NO: 20) converted the antagonist mEGF$_{(33-42)}$ into an agonist. This residue substitution generates a predicted conformation unlikely to be able to form H-bonds. Although both receptor binding and adhesion responses were retained in this peptide the loss of antagonism would suggest that H-bonding between tyrosine (P5) and the arginine (P9) is important for these antagonist activities.

Modelling studies suggested that citrulline (an uncharged arginine mimetic) would also be capable of forming this H-bonded motif.

It was found that replacement of arginine (P9) with citrulline (peptide IV) (SEQ ID NO: 19) increased both receptor binding and inhibition of attachment to laminin substrata whilst retaining antagonist migratory response (Table 1a), reinforcing the observation that it is not the positive charge that is required rather than an active conformation generated by hydrogen bonding. These findings thus identify H-bonding between P5 and P9 as being more important than the charge at the P9 arginine in determining antagonist activity. Subsequent strategies involved the substitution of variant residues in the antagonistic mEGF$_{(33-42)}$ with those present in the agonistic Lam.β-1$_{(925-933)}$ sequence (peptides I–III) (SEQ ID NO: 16, 17 AND 18), in an effort to identify key amino acids in the C-terminal regions (P5–10) of the two ligands responsible for their contrasting bioactivities.

Substitution of isoleucine (P6) for serine (peptide I) (SEQ ID NO: 16) resulted in both reduced receptor affinity and potency in displacement of cell adhesion to laminin. However, this analogue retained weak antagonist activities in the motility assay. It is therefore of interest that studies on the YIGSR sequence (SEQ ID NO: 28) indicate that residue substitution, at the position taken by isoleucine in the pentapeptide, are well tolerated and may increase potency (Kawasaki et al 1994).

Replacement of aspartate (P8) with serine (peptide II) (SEQ ID NO: 17) resulted in a complete loss of biological function. as did peptide III (SEQ ID NO: 18) encompassing both the former (isoleucine (P6) for serine) and latter (serine (P8) for aspartate) substitutions. Since this mEGF$_{(33-42)}$ analogue sequence (peptide II) (SEQ ID NO: 17) encompasses the active YIGSR amino acid sequence (SEQ ID NO: 28) agonist, it is suggested that this loss of activity may be attributed to the valine (P2) and isoleucine (P3) residues in the N-terminal half of mEGF$_{(33-42)}$. Alternatively, addition of a C-terminal cysteine to the YIGSR sequence (SEQ ID NO: 28) is known to reduce potency (Kawasaki et al 1994). Additional peptides incorporating the valine (P2) and isoleucine (P3) substitutions are currently under investigation.

The determination of the minimum core peptide structure is ongoing and involves similar characterisation studies on a number of sequences truncated at the C-terminal.

These studies have thus identified an important antagonist of 67-LR mediated activities in peptide IV (SEQ ID NO: 19). The sequence, (AcC(Acm)-VIGYSGD-[Cit]-C-(Acm)-NH$_2$.) (SEQ ID NO 19), may provide an important template for anti-angiogenic drugs in that it is resistant to cleavage by trypsin-like proteases and has been identified as being more potent than mEGF$_{(33-42)}$ in screening procedures.

Advantages

The advantages of the invention, and the ways in which disadvantages of previously known arrangements are overcome include:
1. Unlike the native 67LR ligand (laminin β-1$_{925-933}$), which is angiogenic in human models, the mEGF$_{33-42}$-derived agents are anti-angiogenic in human models.
2. mEGF$_{33-42}$ has the advantage of inhibiting both laminin- and EGF-stimulated angiogenesis.
3. mEGF$_{33-42}$ prevents tumour cell attachment to basement membranes.

What is claimed is:

1. A synthetic peptide factor comprising the amino acid sequence SEQ ID NO:2 wherein:
   a) said sequence is modified such that at least one of i) SEQ ID NO:2 tyrosine amino acid residue 5 and ii) SEQ ID NO:2 arginine amino acid residue 9 are substituted, wherein said tyrosine amino acid residue 5 is substituted with a tyrosine analogue, and said arginine amino acid residue 9 is substituted with an arginine analogue; and
   b) the synthetic peptide factor binds to laminin receptors.

2. The synthetic peptide factor of claim 1, having an N-terminal amino acid residue and a C-terminal amino acid residue, wherein the N-terminal amino acid residue is chemically modified by the addition of an amino acid capping moiety, the C-terminal amino acid residue is chemically modified by the addition of an amino acid capping moiety, or a cysteine residue thiol group is chemically modified by the addition of an amino acid capping moiety to the cysteine residue thiol group.

3. The synthetic peptide factor of claim 2, wherein the SEQ ID NO:2 tyrosine residue 5 is substituted by tetrahydroisoquinoline-3-carboxylic acid.

4. The synthetic peptide factor of claim 2, wherein the SEQ ID NO:2 arginine residue 9 is substituted by citrulline.

5. The synthetic peptide factor of claim 1, wherein the SEQ ID NO:2 tyrosine residue 5 is substituted by tetrahydroisoquinoline-3-carboxylic acid.

6. The synthetic peptide factor of claim 1, wherein the SEQ ID NO:2 arginine residue 9 is substituted by citrulline.

7. A synthetic peptide factor comprising the amino acid sequence SEQ ID NO:2, said peptide factor having an N-terminal amino acid residue and a C-terminal amino acid residue, wherein
   a) said sequence is modified by at least one first modification and optionally by at least one second modification; and
   b) the synthetic peptide factor binds to laminin receptors, wherein said first modification is selected from the group consisting of: substitution of SEQ ID NO:2 tyrosine amino acid residue 5 with a tyrosine analogue and substitution of SEQ ID NO: 2 arginine amino acid residue 9 with an arginine analogue; and
   wherein said second modification is selected from the group consisting of chemical modification of the N-terminal amino acid residue by the addition of an amino acid capping moiety; chemical modification of the C-terminal amino acid residue by the addition of an amino acid capping moiety; chemical modification of a cysteine residue thiol group by the addition of an amino acid capping moiety to the cysteine residue thiol group; replacement of a peptide bond with a protease-resistant peptide bond isostere; replacement of a glycine residue with an α,α-dialkyl substituted amino acid; and stabilisation of a helical turn of the peptide using suitable intra chain linkers.

8. The synthetic peptide factor according to claim 7, wherein the SEQ ID NO:2 tyrosine amino acid residue 5 is substituted by tetrahydroisoquinoline-3-carboxylic acid.

9. The synthetic peptide factor according to claim 7 wherein the SEQ ID NO:2 arginine amino acid residue 9 is substituted by Citrulline.

10. A synthetic peptide factor comprising the amino acid sequence SEQ ID NO:2, said peptide factor having an N-terminal amino acid residue and a C-terminal amino acid residue, wherein
   a) said sequence is modified by a first modification and by at least one second modification; and
   b) the synthetic peptide factor binds to laminin receptors, wherein said first modification is selected from the group consisting of substitution of SEQ ID NO:2 tyrosine amino acid residue 5 with a tyrosine analogue and substitution of SEQ ID NO: 2 arginine amino acid residue 9 with an arginine analogue; and
   wherein said second modification is selected from the group consisting of: chemical modification of the N-terminal amino acid residue by the addition of an amino acid capping moiety; chemical modification of the C-terminal amino acid residue by the addition of an amino acid capping moiety; chemical modification of a cysteine residue thiol group by the addition of an amino acid capping moiety to the cysteine residue thiol group; replacement of a peptide bond with a protease-resistant peptide bond isostere; replacement of a glycine residue with an α,α-dialkyl substituted amino acid; and stabilisation of a helical turn of the peptide using suitable intra chain linkers.

11. A method of antagonizing a laminin receptor in a patient, the method comprising the step of
   administering to the patient a medicament comprising a synthetic peptide factor comprising the amino acid sequence SEQ ID NO:2 in an amount effective to bind the laminin receptor as an antagonist, wherein said sequence is modified such that SEQ ID NO:2 arginine amino acid residue 9 is substituted with an arginine analogue.

12. The method of claim 11, wherein said synthetic peptide has having an N-terminal amino acid residue and a C-terminal amino acid residue is further modified, wherein the N-terminal amino acid residue is chemically modified by the addition of an amino acid capping moiety, the C-terminal amino acid residue is chemically modified by the addition of an amino acid capping moiety, or a cysteine residue thiol group is chemically modified by the addition of an amino acid capping moiety to the cysteine residue thiol group.

13. The method of claim 12, wherein the SEQ ID NO:2 arginine residue 9 is substituted by citrulline.

14. A method of agonizing a laminin receptor in a patient, the method comprising the step of
   administering to the patient a medicament comprising a synthetic peptide factor comprising the amino acid sequence SEQ ID NO:2 in an amount effective to bind the laminin receptor as an agonist, wherein said sequence is modified such that SEQ ID NO:2 tyrosine amino acid residue 5 is substituted with a tyrosine analogue.

15. The method of claim 14 wherein said medicament is for promoting wound healing.

16. The method according to claim 14 wherein said medicament is for treating retinopathy of prematurity.

17. The method of claim 14, wherein said synthetic peptide having an N-terminal amino acid residue and a C-terminal amino acid residue is further modified, wherein the N-terminal amino acid residue is chemically modified by the addition of an amino acid capping moiety, the C-terminal amino acid residue is chemically modified by the addition of an amino acid capping moiety, or a cysteine residue thiol group is chemically modified by the addition of an amino acid capping moiety to the cysteine residue thiol group.

18. The method of claim 17, wherein the SEQ ID NO:2 tyrosine residue 5 is substituted by tetrahydroisoquinoline-3-carboxylic acid.

19. The method of claim 17 wherein said medicament is for treatment of retinopathy of prematurity.

20. A method of antagonizing a laminin receptor in a patient, the method comprising the step of
administering to the patient a medicament comprising a synthetic peptide factor in an amount effective to bind the laminin receptor as an antagonist, wherein said peptide factor comprises the amino acid sequence SEQ ID NO:2, said peptide factor having an N-terminal amino acid residue and a C-terminal amino acid residue;
wherein said sequence is modified by a first modification and optionally by at least one second modification;
wherein said first modification is substitution of arginine amino acid residue 9 with an arginine analogue; and
wherein said second modification is selected from the group consisting of: chemical modification of the N-terminal amino acid residue by the addition of an amino acid capping moiety; chemical modification of the C-terminal amino acid residue by the addition of an amino acid capping moiety; chemical modification of a cysteine residue thiol group by the addition of an amino acid capping moiety to the cysteine residue thiol group; replacement of a peptide bond with a protease-resistant peptide bond isostere; replacement of a glycine residue with an $\alpha,\alpha$-dialkyl substituted amino acid; and stabilization of a helical turn of the peptide using suitable intra chain linkers.

21. A method of agonizing a laminin receptor in a patient, the method comprising the step of
administering to the patient a medicament comprising a synthetic peptide factor in an amount effective to bind the laminin receptor as an agonist, wherein said peptide factor comprises the amino acid sequence SEQ ID NO:2, said peptide factor having an N-terminal amino acid residue and a C-terminal amino acid residue;
wherein said sequence is modified by a first modification and optionally by at least one second modification;
wherein said first modification is substitution of SEQ ID NO:2 tyrosine amino acid residue 5 with a tyrosine analogue; and
wherein said second modification is selected from the group consisting of: chemical modification of the N-terminal amino acid residue by the addition of an amino acid capping moiety; chemical modification of the C-terminal amino acid residue by the addition of an amino acid capping moiety; chemical modification of a cysteine residue thiol group by the addition of an amino acid capping moiety to the cysteine residue thiol group; replacement of a peptide bond with a protease-resistant peptide bond isostere; replacement of a glycine residue with an $\alpha,\alpha$-dialkyl substituted amino acid; and stabilisation of a helical turn of the peptide using suitable intra chain linkers.

22. The method of claim 21 wherein said medicament is for promoting wound healing.

23. The method according to claim 21 wherein said medicament is for treatment of retinopathy of prematurity.

* * * * *

UNITED STATES PATENT AND TRADEMARK OFFICE
CERTIFICATE OF CORRECTION

PATENT NO.   : 6,995,136 B1
DATED        : February 7, 2006
INVENTOR(S)  : Nelson et al.

It is certified that error appears in the above-identified patent and that said Letters Patent is hereby corrected as shown below:

Column 32,
Line 53, "peptide has having an N-terminal amino acid" should read
-- peptide having an N-terminal amino acid --.

Signed and Sealed this

Eighteenth Day of April, 2006

JON W. DUDAS
*Director of the United States Patent and Trademark Office*

SEQUENCE LISTING

```
<160> NUMBER OF SEQ ID NOS: 31

<210> SEQ ID NO 1
<211> LENGTH: 9
<212> TYPE: PRT
<213> ORGANISM: Artificial Sequence
<220> FEATURE:
<223> OTHER INFORMATION: Artificial Sequence based on linear sequence of
      amino acids 925-933 of mature muring laminin B1 chain
<220> FEATURE:
<221> NAME/KEY: MOD_RES
<222> LOCATION: (9)..(9)
<223> OTHER INFORMATION: AMIDATION

<400> SEQUENCE: 1

Cys Asp Pro Gly Tyr Ile Gly Ser Arg
1               5

<210> SEQ ID NO 2
<211> LENGTH: 10
<212> TYPE: PRT
<213> ORGANISM: Artificial Sequence
<220> FEATURE:
<223> OTHER INFORMATION: Artificial Sequence based on amino acid
      residues 33 to 42 of murine epidermal growth factor (mEGF)

<400> SEQUENCE: 2

Cys Val Ile Gly Tyr Ser Gly Asp Arg Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: tyrosine analogue at position 5

<400> SEQUENCE: 3

Cys Val Ile Gly Xaa Ser Gly Asp Arg Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: arginine analogue at position 9
```

```
<400> SEQUENCE: 4

Cys Val Ile Gly Tyr Ser Gly Asp Xaa Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION

<400> SEQUENCE: 5

Cys Val Ile Gly Tyr Ser Gly Asp Arg Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (10)..(10)
<223> OTHER INFORMATION: AMIDATION

<400> SEQUENCE: 6

Cys Val Ile Gly Tyr Ser Gly Asp Arg Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Acteoamido methyl group
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: AMIDATION
<220> FEATURE:
<221> NAME/KEY: MOD_RES
<222> LOCATION: (10)..(10)
<223> OTHER INFORMATION: Acteoamido methyl group

<400> SEQUENCE: 7

Cys Val Ile Gly Tyr Ser Gly Asp Arg Cys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
```

<223> OTHER INFORMATION: tyrosine analog

<400> SEQUENCE: 8

Cys Val Ile Gly Xaa Ser Gly Asp Arg Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (9)..(9)
<223> OTHER INFORMATION: Citrulline at position 9

<400> SEQUENCE: 9

Cys Val Ile Gly Tyr Ser Gly Asp Xaa Cys
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: 2',6'-dimethyl-beta-methyl-tyrosine at position
      5 of linear sequence of amino acids 925-933 of the mature murine
      b1 chain

<400> SEQUENCE: 10

Cys Asp Pro Gly Xaa Ile Gly Ser Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: 2-O-methyl-tyrosine at position 5 of linear
      sequence of amino acids 925-933 of the mature murine b1 chain

<400> SEQUENCE: 11

Cys Asp Pro Gly Xaa Ile Gly Ser Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: 2-O-ethyl-tyrosine at position 5 of linear
      sequence of amino acids 925-933 of the mature murine b1 chain

<400> SEQUENCE: 12

Cys Asp Pro Gly Xaa Ile Gly Ser Arg
1               5

```
<210> SEQ ID NO 13
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: tyrosine analog
<220> FEATURE:
<221> NAME/KEY: MISC_FEATURE
<222> LOCATION: (9)..(9)
<223> OTHER INFORMATION: Citrulline at position 9 of sequence based on
      mEGF 32-42

<400> SEQUENCE: 13

Cys Val Ile Gly Xaa Ser Gly Asp Xaa Cys
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DISULFID
<222> LOCATION: (1)..(10)
<223> OTHER INFORMATION: Disulphide bond betwen N and C terminal
      cysteines of sequence based on mEGF 33-42

<400> SEQUENCE: 14

Cys Val Ile Gly Tyr Ser Gly Asp Arg Cys
1               5                   10

<210> SEQ ID NO 15
<211> LENGTH: 20
<212> TYPE: PRT
<213> ORGANISM: Artificial Sequence
<220> FEATURE:
<223> OTHER INFORMATION: Artificial Sequence corresponding to COOH
      terminal end of the human laminin receptor

<400> SEQUENCE: 15

Pro Thr Glu Asp Trp Ser Ala Gln Pro Ala Thr Glu Asp Trp Ser Ala
1               5                   10                  15

Ala Pro Thr Ala
            20

<210> SEQ ID NO 16
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: acetamido methyl group
<220> FEATURE:
<221> NAME/KEY: MOD_RES
<222> LOCATION: (10)..(10)
```

<223> OTHER INFORMATION: AMIDATION

<400> SEQUENCE: 16

Cys Val Ile Gly Tyr Ile Gly Asp Arg Cys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION

<400> SEQUENCE: 17

Cys Val Ile Gly Tyr Ser Gly Ser Arg Cys
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION

<400> SEQUENCE: 18

Cys Val Ile Gly Tyr Ile Gly Ser Arg Cys
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)

```
<223> OTHER INFORMATION: acetamido methyl group
<220> FEATURE:
<221> NAME/KEY: MISC_FEATURE
<222> LOCATION: (9)..(9)
<223> O

```
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION
<220> FEATURE:
<221> NAME/KEY: MOD_RES
<222> LOCATION: (10)..(10)
<223> OTHER INFORMATION: acetamido methyl group

<400> SEQUENCE: 22

Cys Ala Ile Gly Tyr Ser Gly Asp Arg Cys
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION

<400> SEQUENCE: 23

Ala Val Ile Gly Tyr Ser Gly Asp Arg Cys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION

<400> SEQUENCE: 24

Cys Val Ile Gly Tyr Ser Gly Asp Arg Ala
```

-continued

```
<210> SEQ ID NO 25
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetamido methyl group
<220> FEATURE:
<221> NAME/KEY: MOD_RES
<222> LOCATION: (10)..(10)
<223> OTHER INFORMATION: acetamido methyl group
<220> FEATURE:
<221> NAME/KEY: MOD_RES
<222> LOCATION: (10)..(10)
<223> OTHER INFORMATION: AMIDATION

<400> SEQUENCE: 25

Cys Val Ile Gly Tyr Ala Gly Asp Arg Cys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: A biotinylated derivative used to demonstrate
      that mEGF (33-42) bound to the 67kDa laminin receptor
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: acetaamido methyl group
<220> FEATURE:
<221> NAME/KEY: MOD_RES
<222> LOCATION: (10)..(10)
<223> OTHER INFORMATION: acetaamido methyl group
<220> FEATURE:
<221> NAME/KEY: MOD_RES
<222> LOCATION: (11)..(11)
<223> OTHER INFORMATION: AMIDATION
<220> FEATURE:
<221> NAME/KEY: MOD_RES
<222> LOCATION: (11)..(11)
<223> OTHER INFORMATION: biotinylation

<400> SEQUENCE: 26

Cys Val Ile Gly Tyr Ser Gly Asp Arg Cys Lys
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Artificial Sequence of concencus sequence which
      presents an acceptable motif for 67-LR activation by both mEGF
      (33-42) Laminin B1 (925-933)
<220> FEATURE:
<221> NAME/KEY: MISC_FEATURE
<222> LOCATION: (3)..(3)
<223> OTHER INFORMATION: substitute amino acid residue or amino acid
      analogue at position 3
```

```
<220> FEATURE:
<221> NAME/KEY: MISC_FEATURE
<222> LOCATION: (5)..(5)
<223> OTHER INFORMATION: substitute amino acid residue or amino acid
      analogue at position 5

<400> SEQUENCE: 27

Gly Tyr Xaa Gly Xaa Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic construct

<400> SEQUENCE: 28

Tyr Ile Gly Ser Arg
1               5

<210> SEQ ID NO 29
<211> LENGTH: 10
<212> TYPE: PRT
<213> ORGANISM: Artificial Sequence
<220> FEATURE:
<223> OTHER INFORMATION: Artificial Sequence of mEGF 33-42 with glycine
      residues replaced in turn by a.a- dialkyl substituted amino acids
      (a-amino isobutyric acid AIB)
<220> FEATURE:
<221> NAME/KEY: MISC_FEATURE
<222> LOCATION: (4)..(4)
<223> OTHER INFORMATION: a-amino isobutyric acid (AIB)
<220> FEATURE:
<221> NAME/KEY: MISC_FEATURE
<222> LOCATION: (7)..(7)
<223> OTHER INFORMATION: a-amino isobutyric acid (AIB)

<400> SEQUENCE: 29

Cys Val Ile Xaa Tyr Ser Xaa Asp Arg Cys
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Artificial Sequence of mEGF 33-42 with glycine
      residues replaced in turn by a.a- dialkyl substituted amino acids
      (aminocyclopropane carboxylic acid ACPCA)
<220> FEATURE:
<221> NAME/KEY: MISC_FEATURE
<222> LOCATION: (4)..(4)
<223> OTHER INFORMATION: aminocyclopropane carboxylic acid (ACPCA)
<220> FEATURE:
<221> NAME/KEY: MISC_FEATURE
<222> LOCATION: (7)..(7)
<223> OTHER INFORMATION: aminocyclopropane carboxylic acid (ACPCA)

<400> SEQUENCE: 30

Cys Val Ile Xaa Tyr Ser Xaa Asp Arg Cys
1               5                   10

<210> SEQ ID NO 31
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
```

-continued

```
<222> LOCATION: (5)..(5)
<223> OTHER INFORMATION: tyrosine analog

<400> SEQUENCE: 31

Cys Asp Pro Gly Xaa Ile Gly Ser Arg
1               5
```